United States Patent [19]
Ball et al.

[11] 4,100,536
[45] Jul. 11, 1978

[54] BIO-ALARM SECURITY SYSTEM

[75] Inventors: Thomas S. Ball, 1637 Butternut Way, Diamond Bar, Calif., 91711; John D. Rugh, Claremont, Calif.

[73] Assignee: Thomas S. Ball, Diamond Bar, Calif.

[21] Appl. No.: 730,376

[22] Filed: Oct. 7, 1976

[51] Int. Cl.² .............. A61B 5/02; G08C 19/26; G08C 19/36
[52] U.S. Cl. .............. 340/207 R; 128/2.05 P; 340/201 P; 340/539; 340/574
[58] Field of Search .............. 340/207 R, 277, 279, 340/224, 206, 201 P; 325/118, 113, 55; 128/2.05 P, 2.06 F, 2.1 A

[56] References Cited

U.S. PATENT DOCUMENTS

| | | | |
|---|---|---|---|
| 2,135,476 | 11/1938 | Rugh | 340/277 |
| 3,210,747 | 10/1965 | Clynes | 340/206 |
| 3,394,370 | 7/1968 | Harper | 340/373 |
| 3,572,316 | 3/1971 | Vogelman et al. | 340/207 |
| 3,603,881 | 9/1971 | Thornton | 325/118 |
| 3,815,109 | 6/1974 | Carraway | 340/207 |
| 3,902,478 | 9/1975 | Konopasek et al. | 340/224 |
| 3,949,388 | 4/1976 | Fuller | 128/2.1 A |
| 3,972,320 | 8/1976 | Kalman | 128/2.1 A |
| 3,993,047 | 11/1976 | Peek | 128/2.05 P |

*Primary Examiner*—Donald J. Yusko
*Attorney, Agent, or Firm*—Lyon & Lyon

[57] ABSTRACT

Disclosed herein is a bio-alarm security system particularly adapted for use in banks for activating an alarm during a robbery without the need for affirmative voluntary action by an employee which might be prevented by the person committing the crime. The system includes one or more pulse rate detectors which are worn by employees, an amplifier and transmitter for transmitting the heart rate or rates to a receiving station where the heart rate signals are monitored. If abnormally fast heartbeat rates are detected such as would be caused by the stress of a robbery, an alarm is activated.

9 Claims, 5 Drawing Figures

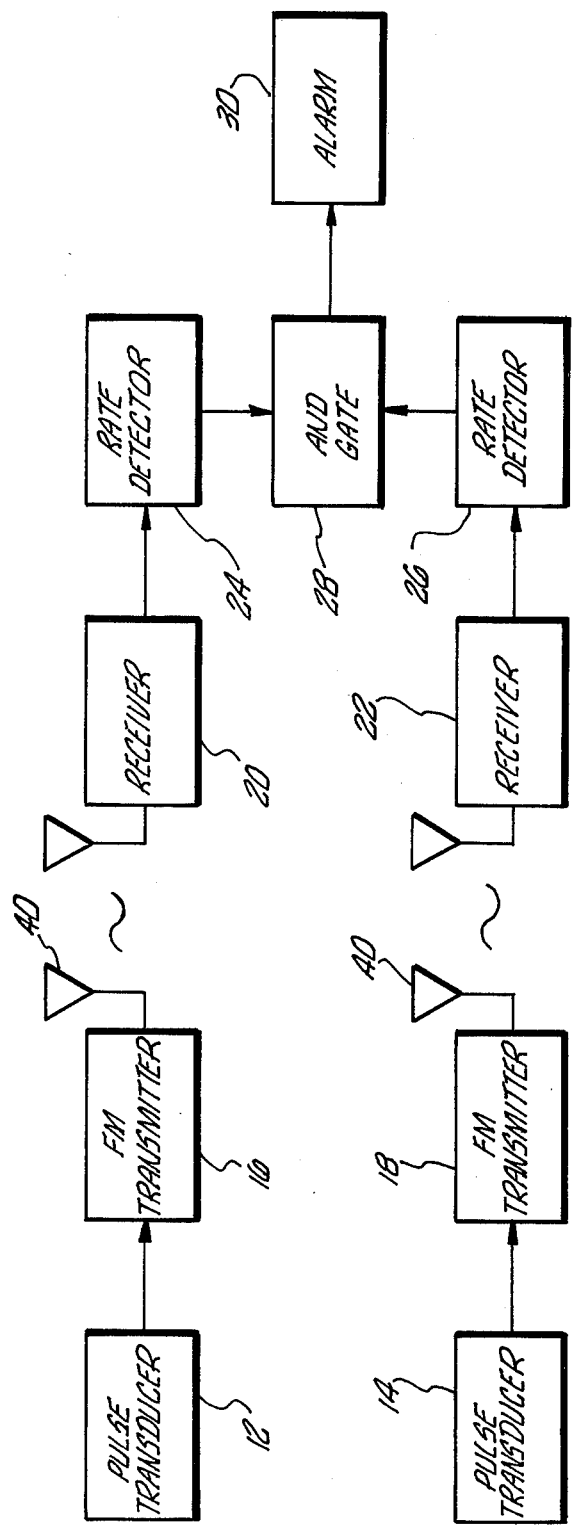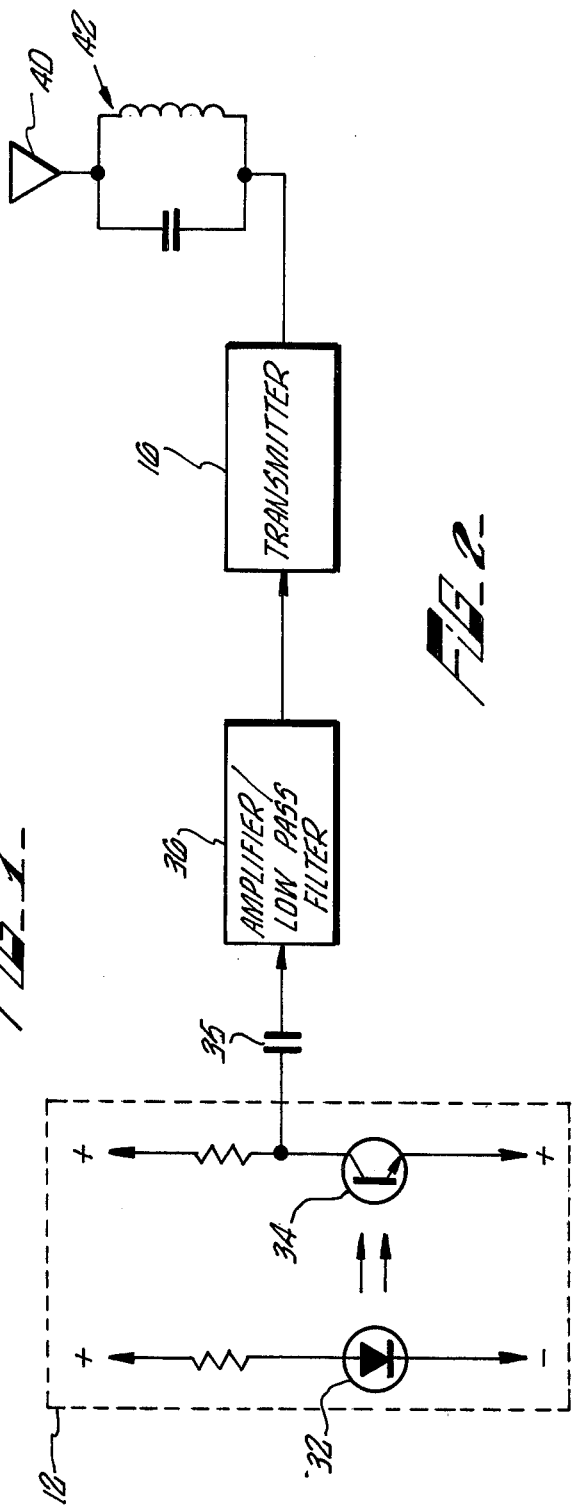

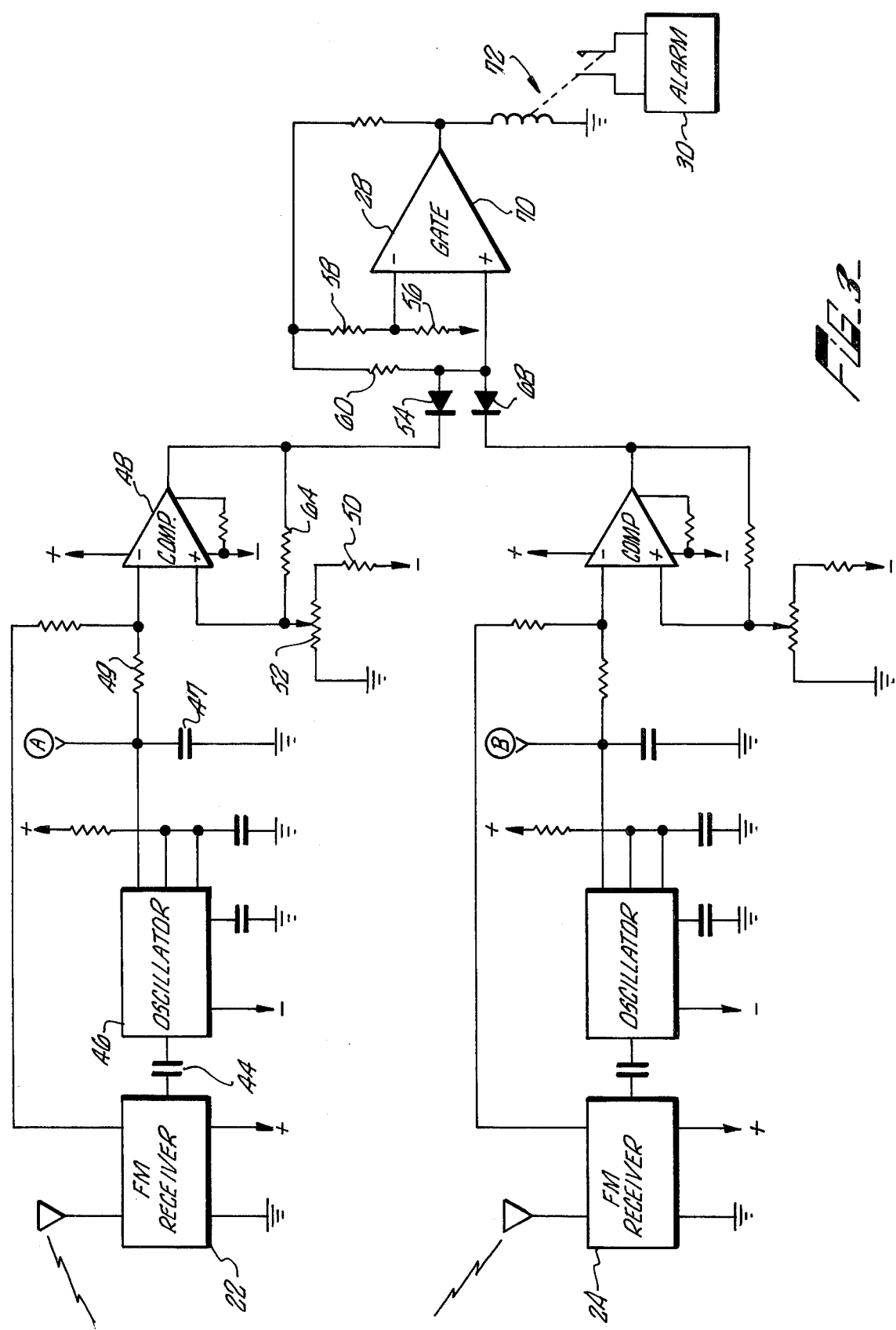

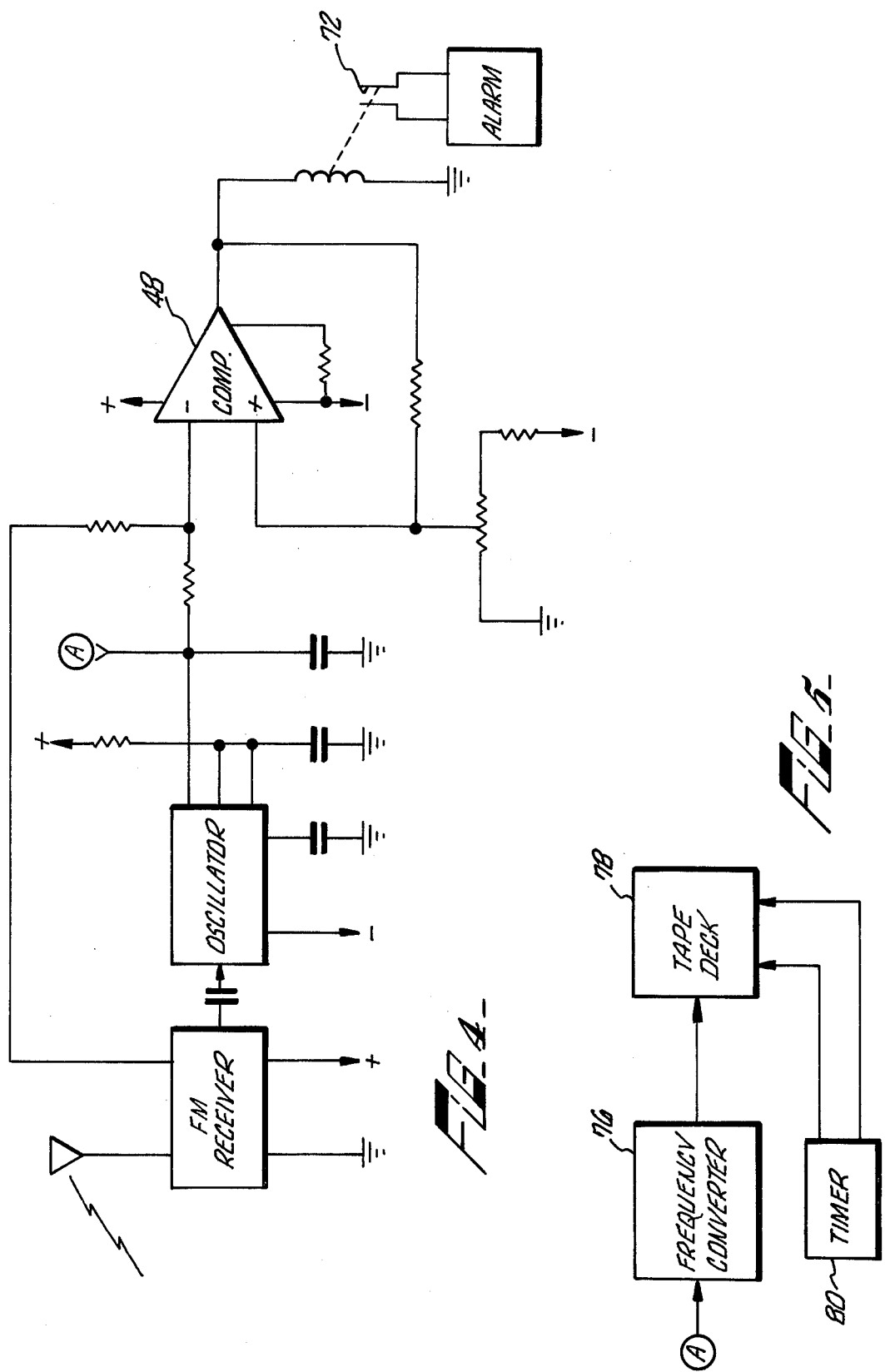

BIO-ALARM SECURITY SYSTEM

BACKGROUND OF THE INVENTION

The security systems generally employed in banks and other commercial businesses highly susceptible to armed robbery include primarily photographic cameras and hidden pushbutton alarms. While the cameras are in continual operation and do not require activation at the time of a robbery, they do not sound any alarm but merely photograph the proceedings for subsequent use in identifying the suspects. The hidden buttons which do activate an alarm and consequently might successfully thwart a robbery attempt or lead directly to the apprehension of its perpetrators, must be voluntarily actuated by an employee to sound the alarm. It is therefore possible through the threat of bodily harm to prevent someone from depressing the alarm button and thereby successfully circumvent the system. Because alarm systems can be circumvented in this manner, their effectiveness as a deterrent to such criminal activity is greatly reduced. If a system could be devised whereby an alarm could be sounded during the commission of a robbery without the need of affirmative action by the person or persons being robbed, many such robberies could be prevented, not only through the utilization of such a system to interrupt robberies in progress or to lead to the immediate apprehension of the persons committing the robberies but also through the public awareness of the system which would act as a substantial deterrent to anyone contemplating such activity. If people knew that an alarm would be sounded the minute they attempted to rob a bank or other establishment, they would be much less likely to attempt the crime.

When a person is subjected to significant levels of psychological stress and tension as would occur during a robbery, certain physiological effects are seen to occur. The effects include an elevated heart rate, increased stomach motility, elevated blood pressure, pupil dilation and changes in one's galvanic skin response. Each of the effects are involuntary responses which could not be prevented from occurring by a person perpetrating a robbery. If an alarm system could utilize one or more of these involuntary responses to activate an alarm it would present a very real deterrent to such crimes. Such a system is disclosed herein.

SUMMARY OF THE INVENTION

Briefly, the invention comprises an alarm system which is activated by physiological changes resulting from a situation of high psychological stress and tension such as that generated during a robbery. The system includes a pair of pulse rate detectors, an amplifier and transmitter for transmitting the heartbeat signals to a receiver where the heart rates are monitored. If the heartbeat rates become substantially elevated over an established normal pattern for the persons being monitored, an alarm is immediately activated without the need for any affirmative physical action.

It is the primary object of the present invention to provide an alarm system for use in banks and the like which is activated during a robbery without the need for any affirmative physical action.

It is another object of the present invention to provide an alarm system which is activated by a physiological effect resulting from a situation of high psychological stress and tension such as that which results during a robbery.

It is a further object of the present invention to provide an alarm system which cannot be circumvented by action taken by a person during the commission of a robbery.

These and other objects and advantages of the present invention will become apparent from the following detailed description taken in conjunction with the accompanying drawings.

DESCRIPTION OF THE PREFERRED EMBODIMENT

FIG. 1 is a block diagram of the bio-alarm security system.

FIG. 2 is a circuit diagram of the pulse transducer and transmitting portion of the bio-alarm security system.

FIG. 3 is a circuit diagram of the signal receiving, comparison and alarm control portion of the bio-alarm security system.

FIG. 4 is a circuit diagram of a single channel embodiment of the system.

FIG. 5 is a block diagram of a recording system for use in the system.

Referring now in detail to the drawings, in the preferred embodiment of the invention the pulse rate is used as an indicia of psychological arousal and false alarms are minimized by requiring that this physiological symptom occur within two employees within a given time to activate the alarm as opposed to an elevated heartbeat rate of a single employee. Referring specifically to FIG. 1, showing the schematic arrangements of units of apparatus for carrying out the present invention, a pair of pulse transducers 12 and 14 are secured to two employees. The pulse rate of the two employees detected by the transducers are transmitted by FM transmitters 16 and 18 to receivers 20 and 22 preferably located in a security area. The signals are then fed to rate detectors 24 and 26 where the heartbeat rates are compared with the normal rates for the two employees which have been studied and recorded over a period of time under working conditions. A comparative signal is then delivered to the AND gate 28 from each detector.

If one or neither of the signals indicate a heartbeat rate greater than the predetermined normal rate for each employee, the output of the AND gate is low indicating normal operation. If, however, both heartbeat rates are above the normal rates, a high output is given off which activates an alarm 30. As indicated above, by monitoring the pulse rates of two employees the chances of a false alarm are reduced over those present in monitoring the pulse rate increases of only one employee. It will be apparent to those skilled in the art that the embodiment shown could be readily enlarged to monitor the pulse rates of any number of employees.

Referring to FIG. 2, a presently preferred embodiment of the electrical apparatus employed in the heartbeat detection and transmission includes the pulse rate detectors 12 and 14 (only 12 being shown) which are plethysmograph transducer assemblies, each comprised of an infrared light source 32 such as an L.E.D. and a phototransistor 34. Because the circuitry for detecting, transmitting, receiving and comparing the heartbeat rates for each of the two employees is the same, only one circuit will be described. The plethysmograph transducer assembly is quite small and adapted to be secured to the earlobe and worn similarly to an earring. The assembly detects the heartbeat of the wearer by directing infrared light from the light source 32 through the earlobe to the phototransistor 34; the variations in the amount of light received by the phototransistor resulting from the pulsating blood level within the earlobe causing variations in the current flow through the phototransistor. These variations in current flow represent the pulse rate of the employee. Previous plethysmograph transducers have employed visible light energy, however, experimentation indicates that an infrared light source provides a stronger signal, apparently due to the absorption properties of the blood through which the light passes.

The pulse rate signal detected by the plethysmograph transducer assembly 12 is capacitively coupled by the capacitor 35 to an amplifier 36 which also serves as a low pass filter to reduce 60 Hz interference. The amplified signal is used to frequency modulate a crystal controlled low power integrated circuit transmitter 16. The output of the transmitter is coupled to an antenna 40 through a tank circuit 42. The heart rate transmitter assembly is preferably powered by rechargeable batteries (not shown).

Referring to FIG. 3, each heart rate signal is received by an FM receiver 22 which is preferably located in a security area. A single multiplex receiver could be employed in lieu of two receivers 22 and 24 if desired. The FM receiver demodulates the signal and provides a varying DC voltage output which fluctuates with each heartbeat. The signal is coupled via capacitor 44 to an oscillator 46 which is typically a monostable multivibrator and acts as a frequency to voltage converter in converting each input pulse to a DC voltage which is proportional to the rate of the pulse. This frequency to voltage conversion is accomplished by means of the differentiator circuit comprised of a capacitor 47, connected between the output of the oscillator 46 and ground, and a resistor 49 connected between the oscillator output and the negative input to a comparator 48. It should be noted that this method of time-averaging is sufficient since the output of the oscillator is relatively narrow pulses, which for the embodiment shown are negative-going.

The DC voltage is then coupled to the negative input of the comparator 48 through a resistor 49. The voltage at the positive terminal is determined by the variable resistor 52, negative voltage supply 50 and resistor 64 and represents the normal heartbeat rate on the job for the person to whom the plethysmograph assembly is secured plus an additional safety factor to include moments of slight arousal which occur from day to day.

When the voltage at the positive terminal of the comparator 48 is greater (more negative) than that at the negative terminal, a normal situation is seen to exist, i.e., the employee is not overly excited, and a low level signal is given out by the comparator causing the diode 54 of the AND gate 28 to forwardly bias and permit current flow from the voltage supply 56 through resistors 58 and 60, diode 54, resistor 64 and variable resistor 52 to ground. If, however, the employee becomes overly excited, as during a robbery, the elevated heartbeat causes the voltage at the negative terminal of the comparator 48 to exceed that at the positive terminal and a high level voltage is given off by the comparator which back-biases the diode and prevents current flow through the diode. When both diode 54 and 68 of the second circuit are back-biased (both employees are excited), comparator 70 to which the anodes of both diodes 54 and 68 are connected, is triggered, energizing a relay 72 which activates an alarm 30. If only one of the employees becomes excited, the voltage supply 56 is grounded in the second circuit and the alarm is not activated. In the preferred embodiment, the receiver, comparator and gate circuits are powered by 110 AC line voltage (PS) but shift automatically to battery power in case of line power failure.

It should also be noted that if one heartbeat rate signal is missing and the other heartbeat rate exceeds its preset threshold, or if both signals are missing, the relay 72 is closed activating the alarm. In the first case, the receiver 22 detects the missing carrier signal from the pulse rate transmitter 12 and provides a signal to the negative input terminal of comparator 48 through resistor 49. When the remaining channel indicates an emergency either by a missing signal or excessive pulse rate, this signal activates the comparator in the same manner as a high pulse rate causing diodes 54 and 68 to be back-biased, triggering comparator 70 and energizing the alarm.

In a second embodiment of the invention, only a single person is monitored. In this embodiment, the same heart rate detection and transmission apparatus is employed, but, as seen in FIG. 4, the receiving end is simplified in that the gate circuitry is not needed and the output from the comparator 48 directly drives the output relay 72. Utilizing this embodiment of the invention, if a single employee becomes psychologically aroused beyond the preset limit manifested by the physiological response of an elevated heartbeat, the alarm is sounded.

Another feature of the present invention involves the use of a recording system as shown in FIG. 5. By making a periodic record, a person's arousal level could be checked after the occurrence of a robbery. If an employee were involved in the crime, the stress experience during the commission of the robbery may not be sufficient to trigger the alarm, but a check of such recordings would indicate an elevated stress level for perhaps a few days or a week prior to the commission of the crime. This information may be quite helpful in a subsequent investigation. Such a system could, of course, have other implementation wherein it may be desirable to monitor a person's state of arousal to determine when an individual may be under a continual state of stress. One extreme example would be a guard at an underground missile site.

In implementing this feature of the invention, the DC voltage which indicates heart rate at points A or B in FIG. 3 may be applied at point A in the circuit illustrated in FIG. 5. From point A the voltage is fed into a frequency converter 76 wherein the varying DC voltage is converted to a variable frequency which can be recorded on a conventional audio tape recorder 78. The recorder is preferably activated for about two seconds every three minutes or so during the time the employee is working, by a timer 80 to allow relatively long periods of pulse rate information to be stored with a minimum amount of tape being used.

Various other changes and modifications may be made in carrying out the present invention without departing from the spirit and scope thereof. Insofar as these changes and modifications are within the purview of the appended claims they are to be considered as part of the present invention.

I claim:

1. An alarm system comprising: an alarm; means carried by at least two individuals for detecting the state of psychological arousal in said individuals and emitting separate first signals of varying intensity corresponding to said states of arousal; means for transmitting said signals; means for receiving said signals; means for comparing each of said first signals with predetermined signals, each of said predetermined signals being proportional to the normal state of arousal of the individual from which said first signal was emitted; means for activating said alarm in a predetermined response to the totality of such comparisons.

2. The combination of claim 1 wherein said alarm is activated upon at least two of said first signals being greater than said corresponding predetermined signals.

3. The combination of claim 1 wherein said alarm is activated upon one of said first signals being greater than said corresponding predetermined signals and one of said detecting and emitting means failing to emit a first signal.

4. The combination of claim 1 wherein said alarm is activated upon all of said detecting and emitting means failing to emit said first signals.

5. The combination of claim 1 wherein said detecting and emitting means comprise a plurality of plethysmograph transducer assemblies, each of said assemblies being adapted to be worn on the ear of one of said individuals and being comprised of an infrared light source and a phototransistor, said source and phototransistor being disposed on opposite sides of the wearer's earlobe such that variations in the amount of light received by the phototransistor resulting from the pulsating blood level within the earlobe cause variations in the current flow through the phototransistor, said variations being proportional to the pulse rate of the individual.

6. The combination of claim 1 wherein said receiving means converts the signals received thereby into DC voltages proportional to the pulse rate of said individuals; and wherein said comparing means comprise a plurality of comparators, one terminal on each of said comparators being in contact with a voltage source proportional to the normal pulse rate of one of said individuals and a second terminal of each of said comparators being electrically coupled to said DC voltage proportional to the detected pulse rate of the corresponding individual, each of said comparators indicating if said DC voltage is greater than the voltage of said source proportional to the predetermined normal pulse rate of the individual, thereby indicating an aroused state, and means for activating said alarm upon all of said comparators so indicating.

7. The combination of claim 6 wherein said detecting and emitting means comprise a plurality of plethysmograph transducer assemblies, each being adapted to be worn on the ear of one of said individuals and being comprised of an infrared light source and a phototransistor, said source and phototransistor being disposed on opposite sides of the wearer's earlobe such that variations in the amount of light received by the phototransistor resulting from the pulsating blood level within the earlobe cause variations in the current flow through the phototransistor, said variations being proportional to the pulse rate of the individual.

8. The combination of claim 1 wherein each of said detecting and emitting means measures the pulse rate of one of said individuals, and said comparing means compares a first signal proportional to said pulse rate with a predetermined signal proportional to the normal pulse rate of the individual from whom said first signal was emitted.

9. An alarm system comprising: an alarm; a plurality of plethysmograph transducer assemblies each being adapted to be worn on the ear of an individual and being comprised of an infrared light source and a phototransistor, said source and phototransistor being disposed on opposite sides of the wearer's earlobe such that variations in the amount of light received by the phototransistor resulting from the pulsating blood level within the earlobe cause variations in the current flow through the phototransistor, said variations being proportional to the pulse rate of the individual; means for transmitting separate signals varying in intensity corresponding to said variations in current flow; means for receiving said signals and converting said signals into DC voltages proportional to the pulse rates of said individuals; comparing means comprising a plurality of comparators, one terminal on each of said comparators being in contact with a voltage source proportional to the normal pulse rate of one of said individuals and a second terminal on each of said comparators being electrically coupled to said DC voltage proportional to the detected pulse rate of said individual, each of said comparators performing a comparison between said DC voltage and the voltage of said source proportional to the predetermined normal pulse rate of the individual; and means for activating said alarm in a predetermined response to the totality of all such comparisons.

* * * * *